(12) United States Patent
Gabriele et al.

(10) Patent No.: US 8,541,029 B2
(45) Date of Patent: Sep. 24, 2013

(54) ARTICLE AND METHOD FOR FOCUSED DELIVERY OF THERAPEUTIC AND/OR DIAGNOSTIC MATERIALS

(75) Inventors: Peter D. Gabriele, York, PA (US); Michael S. Flemmens, Glen Rock, PA (US); Jeffrey H. Robertson, York, PA (US); Andrew Hogan, Red Lion, PA (US)

(73) Assignee: Armark Authentication Technologies, LLC, Glen Rock, PA (US)

( * ) Notice: Subject to any disclaimer, the term of this patent is extended or adjusted under 35 U.S.C. 154(b) by 0 days.

(21) Appl. No.: 13/337,570

(22) Filed: Dec. 27, 2011

(65) Prior Publication Data

US 2012/0093930 A1 Apr. 19, 2012

Related U.S. Application Data

(60) Division of application No. 12/342,830, filed on Dec. 23, 2008, now abandoned, which is a continuation-in-part of application No. 11/578,695, filed on Oct. 17, 2006.

(60) Provisional application No. 61/017,815, filed on Dec. 31, 2007.

(51) Int. Cl.
*A61K 9/14* (2006.01)
*A61K 39/395* (2006.01)
*A61K 9/22* (2006.01)
*A61F 2/00* (2006.01)

(52) U.S. Cl.
USPC .............. 424/486; 424/130.1; 424/158.1; 424/484; 424/468; 424/426

(58) Field of Classification Search
USPC ............... 424/468, 130.1, 174.1, 484, 158.1, 424/423, 443, 426, 486; 514/296, 629
See application file for complete search history.

(56) References Cited

U.S. PATENT DOCUMENTS

| | | |
|---|---|---|
| 4,640,035 A | 2/1987 | Kind et al. |
| 5,162,074 A | 11/1992 | Hills |
| 5,213,812 A | 5/1993 | Ruiz |
| 5,344,297 A | 9/1994 | Hills |
| 5,466,410 A | 11/1995 | Hills |
| 5,551,588 A | 9/1996 | Hills |

(Continued)

FOREIGN PATENT DOCUMENTS

| | | |
|---|---|---|
| DE | 4412651 A1 | 10/1995 |
| DE | 10143070 A1 | 5/2002 |

(Continued)

OTHER PUBLICATIONS

"Application of PHAs in Medicine and Pharmacy," Simon F. Williams, PhD. and David P. Martin, PhD., www.tepha.com/news-and-events-publications.htm (Jun. 18, 2010).

(Continued)

*Primary Examiner* — Blessing Fubara
(74) *Attorney, Agent, or Firm* — McNees Wallace & Nurick LLC (57) ABSTRACT

A microfiber extrudate and delivery process includes a biocompatible polymer matrix forming a body of the microfiber extrudate, an exogenously excitable material arranged within the body, and an active load arranged within the body.

15 Claims, 6 Drawing Sheets

(56) References Cited

U.S. PATENT DOCUMENTS

| | | | |
|---|---|---|---|
| 5,562,930 A | 10/1996 | Hills | |
| 5,846,565 A | 12/1998 | Brem et al. | |
| 6,376,644 B1 | 4/2002 | Mao et al. | |
| 6,461,586 B1 | 10/2002 | Unger | |
| 6,551,353 B1 | 4/2003 | Baker et al. | |
| 6,858,222 B2 | 2/2005 | Nelson et al. | |
| 6,861,142 B1 | 3/2005 | Wilkie et al. | |
| 6,902,932 B2 | 6/2005 | Altman et al. | |
| 6,974,805 B2 | 12/2005 | Hu | |
| 6,974,862 B2 | 12/2005 | Ringeisen et al. | |
| 6,986,739 B2 | 1/2006 | Warren et al. | |
| 7,033,603 B2 | 4/2006 | Nelson et al. | |
| 7,101,857 B2 | 9/2006 | Sung et al. | |
| 7,209,616 B2 | 4/2007 | Welker et al. | |
| 7,214,765 B2 | 5/2007 | Ringeisen et al. | |
| 7,384,786 B2 | 6/2008 | Freyman et al. | |
| 7,417,112 B2 | 8/2008 | Rathore et al. | |
| 7,418,209 B2 | 8/2008 | Salamon et al. | |
| 7,491,407 B2 * | 2/2009 | Pourdeyhimi et al. | 424/443 |
| 7,492,535 B2 | 2/2009 | Descour et al. | |
| 7,514,095 B2 | 4/2009 | Nelson et al. | |
| 7,524,513 B2 | 4/2009 | Hai-Quan et al. | |
| 2002/0103517 A1 | 8/2002 | West et al. | |
| 2003/0138493 A1 | 7/2003 | Dang | |
| 2004/0067360 A1 | 4/2004 | Steenblik et al. | |
| 2005/0232964 A1 * | 10/2005 | Fennimore, Jr. | 424/423 |
| 2005/0249770 A1 | 11/2005 | Hunter | |
| 2006/0018948 A1 * | 1/2006 | Guire et al. | 424/426 |
| 2007/0154512 A1 | 7/2007 | Dave et al. | |

FOREIGN PATENT DOCUMENTS

| | | |
|---|---|---|
| EP | 1512777 A1 | 3/2005 |
| GB | 2434363 A | 10/2005 |
| JP | 62078206 A | 4/1987 |
| JP | 2003201626 A | 7/2003 |
| WO | 0009088 A1 | 2/2000 |
| WO | 0230472 A2 | 4/2002 |
| WO | 03000237 A2 | 1/2003 |
| WO | 2004050966 A1 | 6/2004 |
| WO | 2007097593 A1 | 8/2007 |
| WO | 2007133807 A2 | 11/2007 |
| WO | 2007134192 A2 | 11/2007 |

OTHER PUBLICATIONS

Kaminski M.D. et al: "Magnetically Responsive Micro Particles for Targeted Drug and Radionuclide Delivery (ANL-03/28)"; ANL Report, [online]; Sep. 2003; pp. 1-94, XP002521520; http://www.ipd.anl.gov/anlpubs/2004/02/48843.pdf; retrieved on Jun. 17, 2009.

Bettinger, Christopher J., et al.: "Enhancement of In Vitro Capillary Tub Formation by Substrate Nanotopography"; Advanced Materials; 2008; pp. 99-103; vol. 20; Wiley-VCH Verlag GmbH & Co., KGaA, Weinheim.

Liu, Hui, et al.: "Three-dimensional Culture for Expansion and Differentiation of Mouse Embryonic Stem Cells"; Biomaterials Journal; 2006; 6004-6014; vol. 27; Elsevier Ltd.; USA.

Bettinger, Christopher J.: "Microfabrication of Poly (Glycerol-Sebacate) for Contact Guidance Applications"; Biomaterials Journal; 2005, pp. 2558-2565; vol. 27; Elsevier Ltd.

Mauro Ferrari: "Cancer Nanotechnology: Opportunities and Challenges"; Nature Reviews: Cancer, vol. 5, Nature Publishing Group (2005).

Foley, John D., et al.: "Cooperative Modulation of Neuritogenesis by PC12 Cells by Topography and Nerve Growth Factor"; Biomaterials Journal; 2004; pp. 3639-3644; vol. 26; Elsevier Ltd.; USA.

Krishnamoorti et al.: "Pathway and Kinetics of Cylinder-to-Sphere Order—Order Transition in Block Copolymers"; Maramolecules 2000, V. 33, pp. 3810-3817, American Chemical Society (2000).

Walboomers, X.F., et al.: "Contact Guidance of Rat Fibroblasts on Various Implant Materials"; J Biomed Mater Res, 47, 1999, pp. 204-212; John Wiley & Sons, Inc. The Netherlands.

Curtis, Adam, et al.: "Topographical Control of Cells"; Biomaterials Journal; 1997; pp. 1573-1583; vol. 18 No. 24; Elsevier Science Limited; Great Britain.

* cited by examiner

ARTICLE AND METHOD FOR FOCUSED DELIVERY OF THERAPEUTIC AND/OR DIAGNOSTIC MATERIALS

CROSS-REFERENCE TO RELATED APPLICATIONS

This application is a division of U.S. application Ser. No. 12/342,830 filed Dec. 23, 2008, which itself claims benefit of and priority to Provisional Application No. 61/017,815, filed Dec. 31, 2007, and U.S. patent application Ser. No. 11/578,695, filed Oct. 17, 2006, all of which are hereby incorporated by reference in their entirety.

FIELD

The present disclosure is generally directed to an article and method for delivering therapeutic and/or diagnostic materials and more particularly to an article and method for focused delivery of pharmaceuticals or other therapeutic materials and/or diagnostic materials to humans and other living organisms.

BACKGROUND

Many diseases, such as cancer, are often pernicious and very aggressive. Treatment is often complicated by the fact that some of the most effective treatment methods can have a deleterious impact on surrounding healthy tissue and cells. As a result, more recent efforts have moved toward therapies which attempt to target only unhealthy cells and thereby minimize the impact on healthy cells.

Hyperthermia is one such approach to cancer therapy. Hyperthermia associated with radiotherapy or chemotherapy is a method for cancer treatment, although the molecular mechanisms of this process are not well understood. Hyperthermia exhibits various anti-tumor effects, including damage of tumor vasculature.

Cancer cells are more sensitive to higher body temperatures than are normal cells. Hyperthermia destroys cancer cells by raising the tumor temperature to a "high fever" range, similar to the way the body uses fever naturally when combating other forms of disease. Because the body's means of dissipating heat is through cooling from blood circulation, sluggish or irregular blood flow leaves cancerous tumor cells vulnerable to destruction at elevated temperatures that are safe for surrounding healthy tissues with normal, efficient blood cooling systems.

Although not wishing to be bound by theory, scientists attribute the destruction of cancer cells at hyperthermic temperatures to damage in the plasma membrane, the cytoskeleton and the cell nucleus. Cancer cells are vulnerable to hyperthermia therapy particularly due to their high acidity caused by the inability to properly expel waste created by anaerobic metabolism. Hyperthermia attacks acidic cells, disrupting the stability of cellular proteins and killing them.

Radiofrequency (RF) hyperthermia is a non-ionizing form of radiation therapy that can substantially improve results from cancer treatment. For chemotherapy drugs that depend on blood transport for delivery, hyperthermia used in combination with chemotherapy (thermo-chemotherapy) enhances blood flow in tumor tissues, increasing the uptake of chemotherapy drugs in tumor membranes. Hyperthermia also induces disassembly of the cytoskeleton, which enlarges the tumor pores for easier drug entry. Once delivered, hyperthermic temperatures can be used as a drug activator, accelerating chemical reactions through heat and drawing essential oxygen molecules to tumor tissue for chemical reaction with the drug. This technology can be designed to optimize those factors that are antagonistic to neoplastic growth.

Several therapies are associated with non-ionizing RF hyperthermic therapy. One is RF ablation where direct radiostimulation of cancerous tissues creates a local intense heat enough to kill neoplastic cells. Another RF approach is to direct RF at nanoparticle targets localized in the tumor site. These nanospheres are affixed with antibodies to focus the delivery of the nanoparticle to the tumor site that then becomes the target of RF stimulation to directly deliver heat to the local tissue. Still another approach is to combine the separate actions of chemotherapeutic agents with tissue hyperthermia.

SUMMARY

In an embodiment of the present disclosure, a microfiber extrudate includes a bio-compatible polymer matrix forming a body of the microfiber extrudate, an exogenously excitable material arranged within the body, and an active load arranged within the body.

In another embodiment of the present disclosure, a discrete exogenously excitable domain includes an exogenously excitable material. The exogenously excitable material is configured to be excited by an exogenous stimulus. The exogenously excitable domain is arranged for positioning in a microfiber extrudate. The microfiber extrudate includes a bio-compatible polymer matrix forming a body of the microfiber extrudate, the exogenously excitable material in a discrete domain within the body.

In another embodiment of the present disclosure, a discrete active load domain includes a therapeutic material. The therapeutic material is configured to be released into a living organism. The active load domain is arranged for positioning in a microfiber extrudate. The microfiber extrudate includes a bio-compatible polymer matrix forming a body of the microfiber extrudate, with the active load arranged as a discrete domain within the body.

In another embodiment of the present disclosure, a microfiber extrudate delivery process includes medically identifying a region for treatment by the active load, administering a microfiber extrudate, and applying the exogenous stimulus to the region for treatment, thereby releasing an active load into the region for treatment. In the embodiment, the microfiber extrudate includes a bio-compatible polymer matrix forming a body of the microfiber extrudate, an exogenously excitable material arranged within the body, and the active load arranged within the body.

In another embodiment of the present disclosure, a microfiber extrudate includes a bio-compatible polymer matrix forming a body of the microfiber extrudate, an exogenously excitable material arranged within the body, and an active load arranged within the body. In the embodiment, the bio-compatible polymer matrix includes a polymer selected from the group consisting of poly(FAD-SA), poly(CCP-SA), poly(FA-SA), poly(EAD-SA), poly glycolide, poly lactic acid, copolymers thereof, and combinations thereof. The exogenously excitable material configured to be excited by an exogenous stimulus is selected from the group of stimuli consisting of radiofrequency excitation, microwave excitation, terahertz excitation, mid infrared excitation, near infrared excitation, visible excitation, ultraviolet excitation, x-irradiation excitation, magnetic excitation, electron beam irradiation excitation, and combinations thereof. The active load has therapeutic properties.

Exemplary embodiments may be used for selectively attacking cancer cells by administering a microfiber extrudate having an exogenously excitable material that may be excited to selectively attack cancer cells while leaving healthy cells intact.

An advantage of the present disclosure includes selectively delivering a therapeutic material, which may, for example, be used for selective attack of cancer cells.

Another advantage of the present disclosure includes selectively delivering a diagnostic material, which may, for example, be used for identifying cancer cells.

Yet another advantage of the present disclosure includes the ability to combine two components that would otherwise impose compositional difficulties into the same structure.

Still another advantage is the diminished effect of an active pharmaceutical ingredient on matrix degradation and diffusion activity.

Another advantage is controlled diffusion of therapeutic and/or diagnostic material in conjunction with the release of material in response to an exogenous stimulus.

Other features and advantages of the present disclosure will be apparent from the following more detailed description of the preferred embodiment, taken in conjunction with the accompanying drawings which illustrate, by way of example, the principles of the disclosure.

BRIEF DESCRIPTION OF THE DRAWINGS

Wherever possible, the same reference numbers will be used throughout the drawings to represent the same parts.

DETAILED DESCRIPTION

Figure 1:
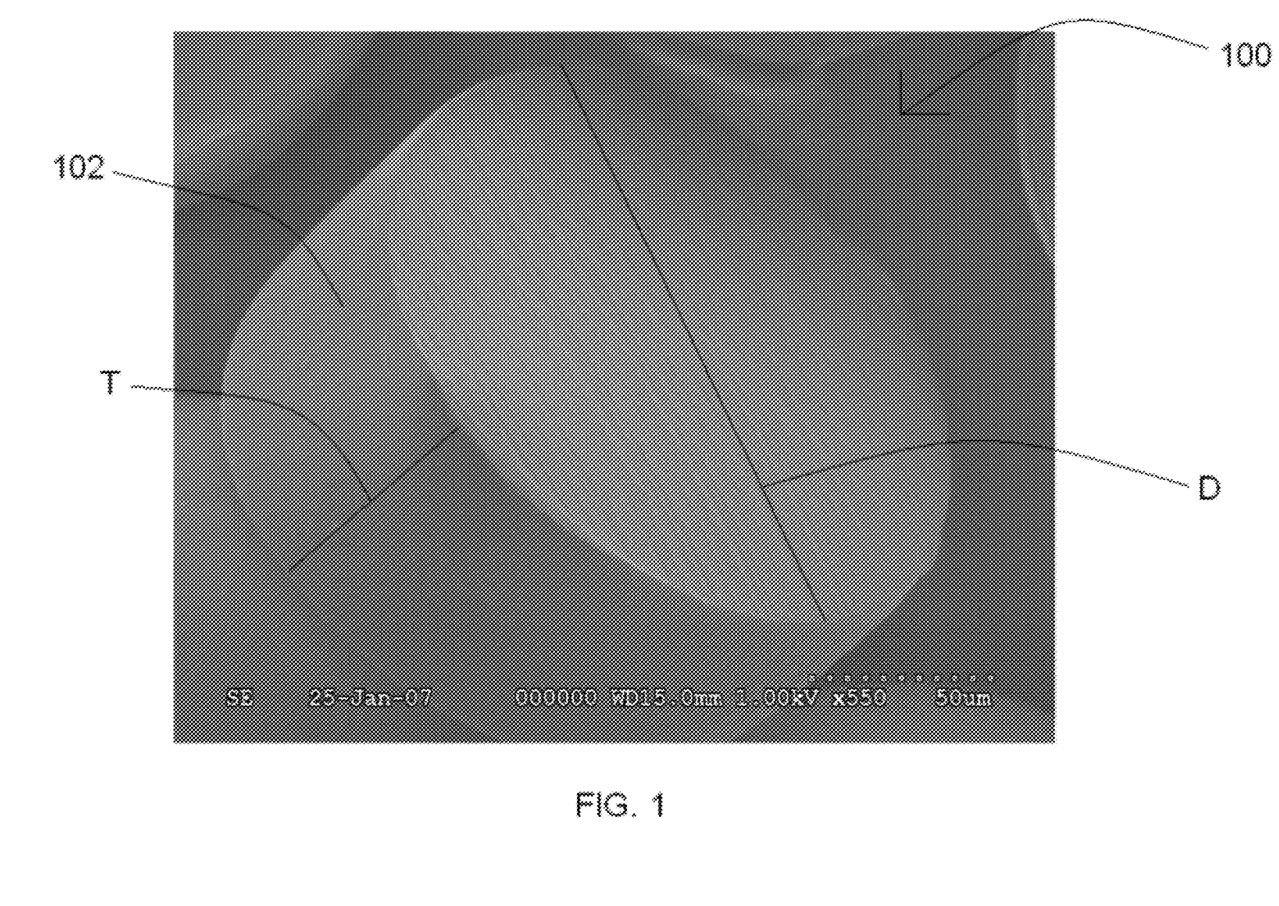
FIG. 1 shows a photograph of an exemplary embodiment of a microfiber extrudate.

FIG. 1 illustrates an exemplary embodiment of a microfiber extrudate 100. The term "microfiber extrudate" as used herein includes microvectors, microcells, microspheres, artificial cells, and other suitable devices. Microfiber extrudate 100 includes a matrix, an exogenously excitable material, and an active load. The matrix forms a body 102 of the microfiber extrudate. Body 102 defines the exterior of microfiber extrudate 100. The body may be, but is not necessarily circular in cross-section and may be designed to have a diameter as small as about 5-10 micrometers or up to about 300 micrometers or larger. As illustrated, body 102 has a diameter D of about 100 micrometers. The body may have a transverse thickness as small as about 5 micrometers or may be elongate or spherical. As illustrated, body 102 has a transverse thickness T of about 10 micrometers.

Figure 2:
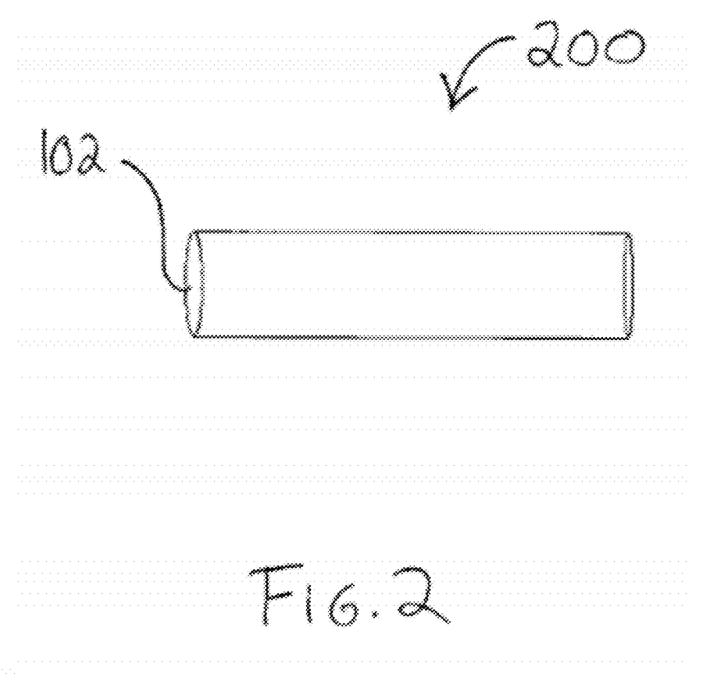
FIG. 2 shows another exemplary embodiment of a microfiber extrudate.

FIG. 2 illustrates another exemplary embodiment of a microfiber extrudate 200. Here, microfiber 200 is elongate. Microfiber extrudate 200 may be transversely sliced along its cross-section to make a plurality of axial slices substantially the same as microfiber extrudate 100. Further, the microfiber extrudate may have a predetermined size and geometry. The design of the microfiber extrudate is spatially resolvable, which permits a deliberate placement of active and passive components within the microfiber extrudate, as will be discussed in more detail herein. Feature size and shape are also controllable, which permits creation of the microfiber extrudate in actual sizes and geometry that correspond to desired sizes and geometries. The predetermined size and geometry may be intended to mimic the size of a cell. For example, the microfiber extrudate may be configured to have a size and geometry similar to a red blood cell or a white blood cell for a specific animal (including humans).

The construction of the microfiber extrudate may be performed using a micro-extrusion fiber spinning process. In this process, a precision engineered die defines intended domains as nano-fiber regions that, when combined at the spinning head, anneal into one single fiber having any number of deliberately defined internal domains. This produces a so-called "island-in-the-sea" arrangement of one or more different materials (e.g., active loads and/or exogenously excitable material) as "islands" within the matrix or "sea" of a base material. Suitable devices and methods for co-extruding a filament of different components in a pre-determined spatial arrangement are described, for example, in U.S. Pat. Nos. 4,640,035; 5,162,074; 5,344,297; 5,466,410; 5,562,930; 5,551,588; and 6,861,142 and in WO 2007/134192, all of which are herein incorporated by reference.

Figure 3:
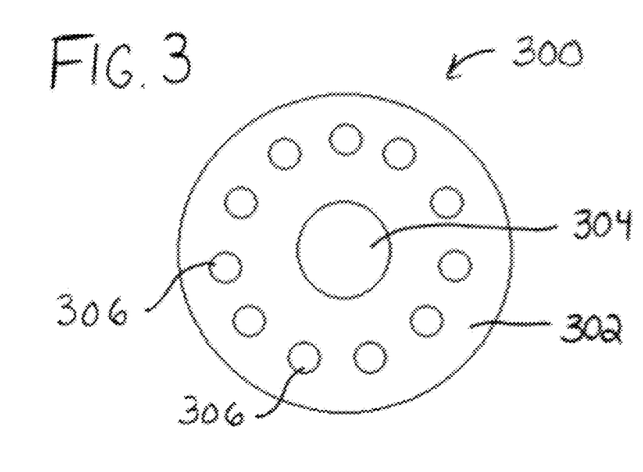
FIG. 3 shows a cross-section of an exemplary embodiment of a microfiber extrudate.
Figure 5:
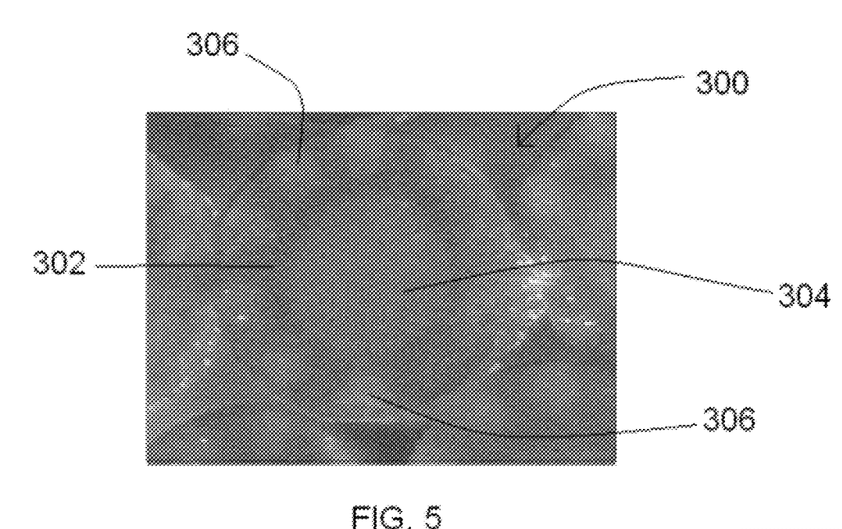
FIG. 5 shows a photograph of an exemplary embodiment of a microfiber extrudate.

The micro-extrusion process includes several extruder barrels that intersect into a specially designed "die head." Each barrel delivers a single component for subsequent combination within the die head. The die head is configured such that the matrix, the exogenously excitable materials, and the active load exiting the multiple extruder barrels enter a series of pixilated stacked die plates, called a die-pack. A unique die-pack may be provided for each different microfiber extrudate design. The total pixel bundle exiting the last plate may contain up to 21,000 or more nano-fibers, which coalesce at the spin head into a single fiber. Referring to FIGS. 3 and 5, a cross-section of a fiber shows the "placement" of domains resulting from the channel directed engineering of the die pack plates.

Once the fibers are produced, they are then bundled into hanks and prepared into blocks, such as by using cellulose solutions in water as a potting media, which are then frozen. The hanks are so oriented to have all long axis structures substantially parallel. The frozen block is preferably mounted in a cryotome such that the blade edge cuts perpendicular to the fibers. Multiple transverse cuts at precise thickness may be made to produce the structure of microfiber extrudate 100.

This process allows the co-fabrication of several material components within the "design space" of the microfiber extrudate. Microfiber extrudate 100 can include three to four material components; more or fewer may be incorporated. The material components can be spatially resolved and freely positioned by design within the body of the microfiber extrudate. It will be appreciated that the microfiber extrudate may be created by co-extruding pure materials for the matrix and each domain, but more typically, the components of the microfiber extrudate may themselves be a mixture of material(s) with the desired properties (for example, the properties of the exogenously excitable materials and/or the active load) arranged in discrete domains or as the matrix, which may assist in the coextrusion of the materials.

Figure 8:
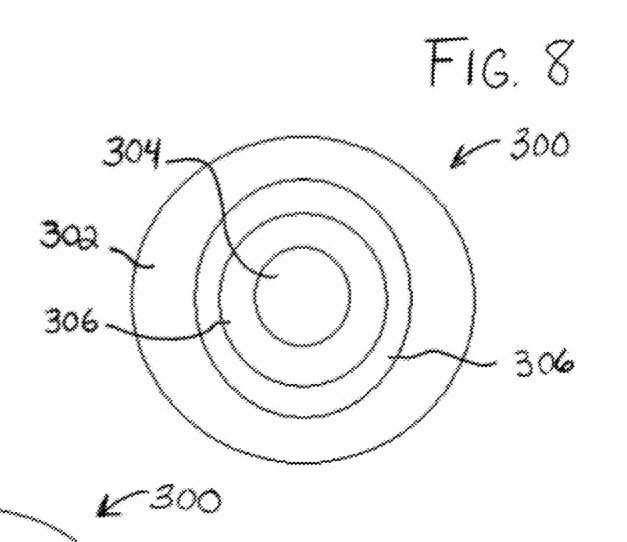
FIG. 8 shows a cross-section of another exemplary embodiment of a microfiber extrudate.
Figure 9:
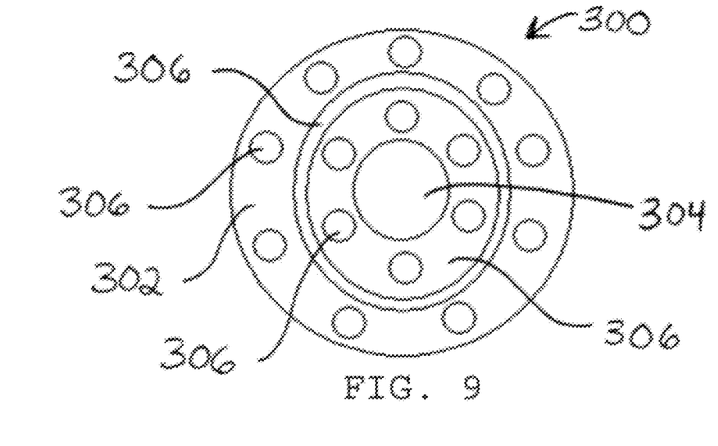
FIG. 9 shows a cross-section of yet another exemplary embodiment of a microfiber extrudate.

FIGS. 3, 8, and 9 show cross-sections of exemplary embodiments of a microfiber extrudate 300. In the embodiments, microfiber extrudate 300 is formed and designed to arrange discrete domains 304, 306 of different materials or combinations of materials, such as an exogenously excitable material and/or an active load within a matrix 302. Each domain can harbor a preferred chemistry for a specific action. Each domain may include the exogenously excitable material, the active load, or a combination of them or other materials. Each domain may also include a certain percent of matrix material to facilitate excitement or to prevent excitement. It will be appreciated the number and location of discrete domains of different materials is exemplary and may be modified depending on the application.

Microfiber extrudate 300 may thus be constructed to include discrete domains with approved excipient materials that contain active pharmaceutical ingredients (API) or a combination of API and inactive or functional domains within the microfiber extrudate. Outside of the domains, the microfiber extrudate may additionally or alternatively include approved excipient materials which contain API, inactive materials or functional materials, or a combination of API and inactive or functional materials. As discussed above, the microfiber extrudate can be designed to have a wide range of sizes (e.g., about 5-10 μm or up to about 300 μm or larger). Consequently, a self-contained drug delivery device in accordance with exemplary embodiments in the size range of circulatory cells can be provided and medically administered intravenously or parenternally.

In an exemplary embodiment, a region for treatment is identified by diagnostic techniques. A microfiber extrudate contains both a therapeutic and an exogenously excitable material is administered to the region for treatment (in some cases, beyond the region for treatment). An exogenous stimulus is then applied to the region of treatment (in some cases, beyond the region for treatment), thereby releasing the active load into the region for treatment. This process can decrease the effect on regions not identified for treatment. In another exemplary embodiment, this process increases the number of healthy cells left intact while attacking the unhealthy cells. In yet another exemplary embodiment, periodic pulses of the exogenous stimulus are applied while the microfiber extrudate is in situ. In administering pain medication, this can replace patient activated intravenous systems for administering pain medicine by providing the patient with control (or limited control) of a device configured to apply the exogenous stimulus. For example, when the patient pushes a button, the exogenous stimulus can be activated, thereby causing pain medicine in the microfiber extrudate to be released into the patient's body.

The API, which may be the active load, may be any therapeutic material. Active pharmaceutical ingredients may include, but are not limited to, ABVD, AVICINE, Acetaminophen, Acridine carboxamide, Actinomycin, Alkylating antineoplastic agent, 17-N-Allylamino-17-demethoxygeldanamycin, Aminopterin, Amsacrine, Anthracycline, Antineoplastic, Antineoplaston, Antitumorigenic herbs, 5-Azacytidine, Azathioprine, BBR3464, BL22, Biosynthesis of doxorubicin, Biricodar, Bleomycin, Bortezomib, Bryostatin, Busulfan, Calyculin, Camptothecin, Capecitabine, Carboplatin, Chlorambucil, Cisplatin, Cladribine, Clofarabine, Cyclophosphamide, Cytarabine, Dacarbazine, Dasatinib, Daunorubicin, Decitabine, Dichloroacetic acid, Discodermolide, Docetaxel, Doxorubicin, Epirubicin, Epothilone, Estramustine, Etoposide, Exatecan, Exisulind, Ferruginol, Floxuridine, Fludarabine, Fluorouracil, 5-Fluorouricil, Fosfestrol, Fotemustine, Gemcitabine, Hydroxyurea, Idarubicin, Ifosfamide, Imiquimod, Irinotecan, Irofulven, Ixabepilone, Lapatinib, Lenalidomide, Liposomal daunorubicin, Lurtotecan, Mafosfamide, Masoprocol, Mechlorethamine, Melphalan, Mercaptopurine, Methotrexate, Mitomycin, Mitotane, Mitoxantrone, Nelarabine, Nilotinib, Nitrogen mustard, Oxaliplatin, PAC-1, Paclitaxel, Pawpaw, Pemetrexed, Pentostatin, Pipobroman, Pixantrone, Polyaspirin, Plicamycin, Procarbazine, Proteasome inhibitor, Raltitrexed, Rebeccamycin, SN-38, Salinosporamide A, Satraplatin, Stanford V, Streptozotocin, Swainsonine, Taxane, Tegafur-uracil, Temozolomide, ThioTEPA, Tioguanine, Topotecan, Trabectedin, Tretinoin, Tris(2-chloroethyl)amine, Troxacitabine, Uracil mustard, Valrubicin, Vinblastine, Vincristine, Vinorelbine, Vorinostat, Zosuquidar, and combinations thereof.

Other therapeutic materials such as anti-tumor antibodies (including VEGH-A or other monoclonal antibodies, for example), antibiotics, bio-agents, bio-pharmaceuticals and/or other suitable therapeutic materials may be included. Additionally or alternatively, diagnostic materials, matrix diffusion control materials, and/or other suitable materials may be included.

The exogenously excitable material is selected to be excited by an exogenous stimulus. The exogenous stimuli include, but are not limited to, radiofrequency excitation, microwave excitation, terahertz excitation, mid infrared excitation, near infrared excitation, visible excitation, ultraviolet excitation, x-irradiation excitation, magnetic excitation, electron beam irradiation excitation, and combinations thereof. Upon receiving the exogenous stimulus, the exogenously excitable material can be excited. The exogenously excitable material may be arranged within the domains in the microfiber extrudate or may be mixed within the microfiber matrix. Various therapies may combine exogenously excitable materials in the microfiber extrudate along with the API.

The microfiber extrudate may include a radiofrequency (RF) sensitive additive as the exogenously excitable material and a degradable polymer as a bio-compatible matrix that can be administered. The exogenously excitable material may be exogenously excited in situ at the local site of tumor angiogenesis, such as a receptor specific region in advancing vascular tissue binding VEGF to facilitate localized heating and thereby denaturing angiogenesis factors and/or destroying abnormal cells at the advancing site. Where the API is the active load, the excitation may be configured to expedite breakdown of the matrix, thus releasing the pharmaceutical more quickly. In RF active embodiments, the microfiber matrix may be formulated with a known additive having a known radiofrequency, lambda max or excitation frequency, which can then be exogenously excited. In another approach, the natural RF response of the cell in the absence of a specific radiosensitive additive is determined by some spectroscopic mechanism like NMR, and a tunable RF generator may be used to administer the exogenous non-ionizing radiation.

An exemplary embodiment of the microfiber matrix includes a radiosensitive active pharmaceutical drug arranged within a polylactide/polyglycolide copolymer prepared as one of four extrudable components. A second component includes the copolymer and an antibody. A third component includes the copolymer and a chemotherapeutic agent. A fourth material is neat copolymer. In another exemplary embodiment, the API is 5-fluorouracil (5-FU), doxorubricin, or acetaminophen.

The matrix of the microfiber extrudate may be any suitable thermoplastic material that is biologically compatible. Generally, suitable bio-compatible matrix material generally falls into one of two primary categories, diffusive or degradable. In primarily diffusive matrix materials, active load components diffuse from its initial domain, through the matrix, and eventually into the environment (e.g., bloodstream or tissue) over time, the rate of which may be enhanced or retarded through exogenous stimulation when an exogenously excitable material is also present. The stimulation may also modify the diffusive profile to increase the amount transmitted. Exemplary diffusive matrix material includes ethyl cellulose polymer, such as that sold by Dow Chemical under the tradename Ethocel.

Degradable material breaks down in body over time, which can be initiated or the rate enhanced, by stimulation in the presence of an exogenously excitable material. Exemplary degradable polymers include poly(FAD-SA), poly(CPP-SA), poly(FA-SA), poly(EAD-SA), poly glycolide, poly lactic acid, copolymers thereof, and combinations thereof. In one embodiment, the microfiber extrudate has a bio-compatible polymer matrix including a polyglycolide/lactide copolymer. In an exemplary embodiment, the matrix is vascular-infusible and bio-compatible material that can be administered parenternally or intravenously into a tumor site to deliver a chemotherapeutic agent released over time as the matrix breaks down. Such a system may also be coupled with antibody technology.

Referring again to FIG. 3, microfiber extrudate 300 includes a matrix depicted as a bio-compatible polymer matrix 302 and a first discrete domain 304 at the core that may contain a suitable bio-active material that may be selected depending upon the desired therapy. As shown in FIGS. 3, 8, and 9, the arrangement of discrete domains 304, 306 and/or polymer matrix 302 can be varied. Varying the arrangement of the discrete domains and/or the polymer matrix can permit additional control of diffusion of materials from the microfiber extrudate and/or degradation of the matrix. Discrete domains 306 of a second material may include the exogenously excitable material depicted as "exogenous activators" demonstrating the ability to custom model the microfiber extrudate to include radiosensitive materials. Referring to FIG. 9, in an exemplary embodiment, microfiber extrudate 300 can be arranged for material in discrete domain 304 to travel through polymer matrix 302 and/or discrete domain 306, thereby permitting staged reactions of materials traveling through the various domains. The staged reactions can be controlled by diffusion and/or by degradation due to the application of exogenous stimulus. Domains susceptible to differing exogenous stimuli can permit the reaction to be further controlled by providing the differing exogenous stimuli at differing times or in differing amounts. In this embodiment, in addition to the timing of the release of material from microfiber extrudate 300, the pathway of the reaction can be controlled.

Additionally or alternatively, domains 306 may include "immunospecific targeting agents" which permits the microfiber extrudate to include antibodies as an active load. While exemplary embodiments are described with respect to cancer therapy, it is contemplated that localized delivery of therapeutic materials in accordance with exemplary embodiments would be useful in the treatment of other diseases, conditions, and disorders by providing different compositions of therapeutic materials, by adjusting the microfiber extrudate size, or other modifications, all of which are within the scope of the invention.

Similarly, the microfiber extrudate may be used for delivering other materials into an animal (including humans) for therapeutic and/or diagnostic purposes. For example, nutrients, vitamins, toxins, poisons, tracers, and/or other components may be included within the domains of the microfiber extrudate to be released upon excitation of the exogenously excitable material. In an exemplary embodiment, toxins may be administered to canines for the purpose of euthanizing. In another exemplary embodiment, a harmless dye that is sensitive to gamma radiation may be administered for the purpose of monitoring exposure to gamma radiation.

In an exemplary embodiment, the body of the microfiber extrudate is an artificial cell-like article for focused therapeutic treatments. One such focused therapeutic treatment is hyperthermic cancer therapy for humans or other animals. The embodiments combine the feature aspects of focused chemotherapy and RF-sensitivity into a single cell-like device that approximates the cellular dimensions of the circulatory system. The artificial cell approach involves combining drug delivery and RF-sensitivity in the microfiber extrudate.

In another exemplary embodiment, the body of the microfiber extrudate is an artificial cell the size of a red or white blood cell and includes API that can degrade over time. The matrix may be selected to expedite or extend the breakdown of the matrix. The matrix may include the exogenously excitable material and, thus, be broken down by exogenous stimulus, thereby releasing the API. Placement of the API (or another active load) and/or the exogenously excitable material active loads may be achieved by using high definition micro-extrusion technology capable of spatially resolving local domains within the microfiber extrudate, as described above.

In a combined system, the microfiber extrudate may deliver a radiofrequency sensitive body and a chemotherapeutic drug. The matrix can be eliminated by resorption following RF excitement. Thus, a single delivery microfiber extrudate acting as an artificial cell combines a controlled drug delivery vehicle (e.g., a red or white blood cell) based on degradable FDA compliant drug delivery polymers (such as but not limited to polyglycolide copolymers), a radiosensitive target material or a radiosensitive chemotherapeutic agent (such as, but not limited to, a fluorinated species), a non-radiosensitive chemotherapeutic agent (such as, but not limited to, 5-fluorouracil), and an optional antibody (such as but not limited to anti-VEGH antibodies) as separate domains of the extrudate. Another embodiment includes a system with indigenous acidic properties like those of cancer cells.

In an exemplary embodiment in which acetaminophen is used as the API active load, the microfiber extrudate can be used for treating melanoma. Because acetaminophen is toxic to the liver, by providing an exogenous stimulus to a region of the body (instead of the whole body) for localized melanoma treatment, the amount of acetaminophen processed by the liver may be lower.

In an exemplary embodiment, a stable, multifunctional microcell acting as a nanocarrier can transport superparamagnetic iron oxide nano-particles (SPIONs) and/or nanoparticle domains for simultaneous diagnostic imaging, hyperthermia or specific therapeutic action, a combination of anti-VEFG antibodies and anti-angiopoietin factors for targeted disruption of angiogenesis, a chemotherapeutic agent, and a microenvironment pH antagonist in a single microfiber extrudate.

In other exemplary embodiments, the microfiber extrudate can be delivered to plants and other living organisms. The exemplary embodiments incorporate ballistic techniques, such as those commonly employed in genetic transformation of crops and other plants for example (e.g., via a gene gun, although the delivery methods described herein are generally not a genetic transformation process per se), to permanently embed microfiber extrudates in plant tissue, which are secured through the use of bio-derived adhesions, such as *Agrobacterium* sp., provided as the discrete domains within the matrix.

Figure 6:
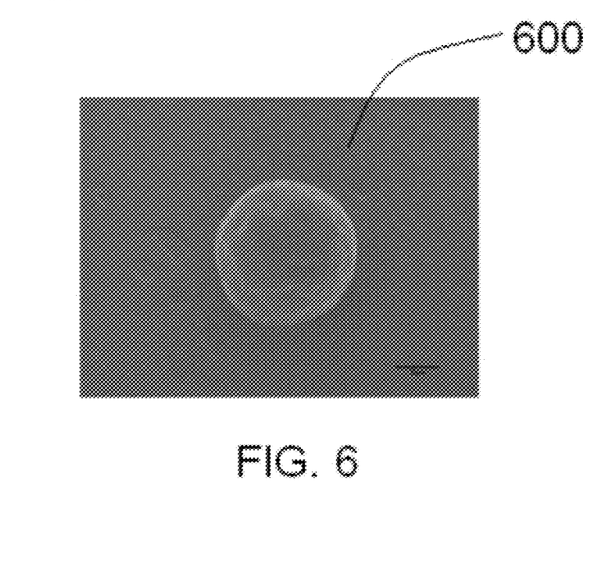
FIG. 6 shows a photograph of an exemplary embodiment of a microfiber extrudate.

In yet another exemplary embodiment, the microfiber extrudate can be treated to transform its shape and/or geometry. The change in shape and/or geometry can include producing a biomimetic delivery system in the natural range of circulatory cells, transforming the entire shape and/or geometry of the microfiber extrudate (for example, transforming the matrix of the microfiber extrudate), and/or transforming the shape and/or geometry of a portion of the microfiber extrudate (for example, transforming the domains in the matrix of the microfiber extrudate). For example, the microfiber extrudate can be transformed from a disc-like microfiber extrudate 100 as shown in FIG. 1 to a sphere-like structure 600 shown in FIG. 6. The matrix of the microfiber extrudate can be configured for transformation in a 50% ethanol and 50% water solution or any other suitable solution. Additionally or alternatively poly ethylene glycol (PEG) can be used. The matrix of the microfiber extrudate can be configured to have increased osmotic potential and may include hypertonic materials, for example, salt, that permit the microfiber extrudate to transform or swell under selected conditions. The transformation into the sphere-like structure may increase the efficacy of a thermally-sensitive active pharmaceutical ingredient. Unexpectedly, the sphere-like microfiber extrudate can generally maintain its sphere-like geometry after being dried. The sphere-like structure can be configured to transform or swell with specific elements of the microfiber extrudate.

The process of converting into the sphere-like structure can permit the microfiber extrudate to incorporate other materials introduced after extrusion. For example, PEG can be used for performing "PEGilation" that brings a suitable material, for example a nano-particle, into the microfiber extrudate. To increase the ability to incorporate other material into the microfiber extrudate, the geometry of the microfiber extrudate may be configured to provide increase surface area and/or decreased surface area. This may be achieved by modifying the extrusion process or by modifying the microfiber extrudate after it is extruded. In an exemplary embodiment, PEGilation can be used for bringing binding agents, such as macrophages, into the microfiber extrudate, thereby permitting the binding agents to be released through diffusion and/or degradation of the matrix. In another exemplary embodiment, PEGilation can used for bringing in material, structures, or nano-particles that prevent white blood cells from attacking the microfiber extrudate. Additionally or alternatively, the microfiber extrudate may be aerosolized.

In other embodiments, the sphere-like structure can be used as or in conjunction with insecticides, fertilizers, degradable applications of controlled release bio-active compounds, taggants, lubricants, sound dampeners, insulators, and/or other suitable applications.

EXAMPLES

A multifunctional, polymeric microfiber extrudate having a dual action payload was created using high definition microextrusion (HDME). An example of HDME is described in the previously referenced publication WO 2007/134192. The microfiber extrudate was modeled for substantially simultaneous noninvasive anti-tumor hyperthermia and drug release. A 75 micrometer (diameter) by 10 micrometer (thickness) microfiber extrudate in the form was a microcell was created by HDME and included an active load of the active pharmaceutical ingredient acetaminophen, an exogenously excitable material of a hyperthermia agent superparamagnetic iron oxide nano-particle (SPION), and a bio-compatible polymer matrix of ethyl cellulose drug delivery polymer (for example, Ethocel®) (Ethocel® is a registered trademark of Dow Chemical, Co., Midland, Mich.). The SPION was susceptible to exogenous excitation from RF.

A second microcell included an active load of acetaminophen as an API, an exogenously excitable material of SPION combined with polylactic acid (PLA), and several different bio-compatible polymer mixtures. The SPION combined with PLA was susceptible to exogenous excitation from microwave RF.

The SPION particle size included in the microcells was 30 micrometers obtained from Rockwood Co. of St. Louis, Mo. The API was USP 99.95% acetaminophen obtained from Sigma-Aldrich, Milwaukee, Wis.

Ethocel® was used as a core stable "passive observer" constituent carrier matrix in an effort to eliminate any contribution a degrading polymer would have on hyperthermia response and drug elution from the matrix. The use of a "passive observer" isolated the hyperthermia and drug elution from any matrix contribution under the influence of RF. Three 75 micrometer by 10 micrometer microcell device samples were prepared by HDME: (1) Ethocel® and SPION identified as Example 1, (2) Ethocel®, SPION, and 10% API identified as Example 2, and (3) neat Ethocel® identified as Example 3 for comparison.

Master batch drug delivery polymer feed stock extrusion pellets were prepared for each of the Examples. At extrusion temperatures the melt flow index of the final polymer feed stocks was 60 grams per minute. The extrusion temperature was set at about 190° C. (about 374° F.). For Example 2, the final theoretical concentration of SPION and API per microcell was determined to be 1.8% by weight and 1.0% by weight, respectively in an Ethocel® matrix showing a loss of 0.8% during cutting. However, as a result of processing loss, the API as determined by UV methods, was 0.85% by weight based on a bulk 500 milligram sampling of microcells.

The micro-spatial cross-sectional resolution and general cross-section die design of the microcells were intended to include selected high concentration spatially resolved domains of SPION/polymer adjacent to API/polymer for microwave induction and local heating within the microcells. The configuration of the die plate through which the molten thermoplastic polymer base stock passed during HDME was produced by photolithography to include about 21,000 individual nanofibrils eventually spun to a final total cross-section design of about 75 micrometers on a heated Godet role and collected on a high speed fiber bobbin.

Fiber on the bobbins was cut perpendicular to fiber spooling to release 8 inches in length parallel fiber hanks. Hanks were bundled in parallel and potted in an aqueous 1% sodium cellulose solution and frozen into about −20° F. (about −28.8° C.) aqueous cellulose bricks. The frozen bricks of parallel fiber hanks were then transversely sliced to about 10 micrometer thickness using a Leika Cryo microtome Model CM-3600 operating at about −10° F. (about 23.3° C.). About 20 grams of each sample was collected. The slices were collected and sieved to 75 micrometers final particle size at room temperature through Retch vertical sieve stacks under continuous aqueous flow. The final particles collected were dried under vacuum for about 24 hours.

The microcells were suspended as an aqueous sample while exposed to microwave RF. Both water and mineral oil were evaluated as a liquid medium to expose microcell samples. 500 milligram samples of each microcell component were dispersed in both water and mineral oil and exposed to 130 watts of microwave RF for 60 seconds to determine the preferred fluid medium to carry out the experiment. As shown in Table 1, temperatures were recorded and illustrate that water had the broadest temperature range response.

TABLE 1

Isolated Temperature Response of Component Materials
(130 Watts for 60 seconds of exposure)

| Material | Dielectric Constant | Initial °F. | P1 60 seconds °F. | ΔT °F. | Thermal Conductivity |
|---|---|---|---|---|---|
| 10 g Mineral Oil | 2.1 | 68 | 68 | 0 | 0.138 Watts/M · K |
| 10 g Deionized Water | 80.4 | 68 | 98 | 30 | 0.600 Watts/M · K |
| 500 mg Ethocel ® 7 in 10 g Water | | 68 | 92 | 24 | — |
| 500 mg Acetaminophen in 10 g Water | | 68 | 90 | 22 | — |
| 500 mg Castor Oil in 10 g Water | | 68 | 90 | 22 | — |
| 500 mg SPION in 10 g Water | | 68 | 115 | 47 | — |
| 500 mg Example 2 in 10 g Water | | 68 | 109 | 41 | — |
| 500 mg Ethocel ® 7 in 10 g Mineral Oil | | 68 | 68 | 0 | — |
| 500 mg Acetaminophen in 10 g Mineral Oil | | 68 | 68 | 0 | — |
| 500 mg Castor Oil in 10 g Mineral Oil | | 68 | 68 | 0 | — |
| 500 mg SPION in 10 g Mineral Oil | | 68 | 75 | 7 | — |
| 500 mg Example 2 in 10 g Mineral Oil | | 68 | 73 | 5 | — |

Surface analysis of samples was performed on a Hitachi® Scanning Electron Microscope Model S-300N with IXRF System Energy Dispersive Spectrometer (EDS). Fiber and microcell slices were examined for the presence of emerging acetaminophen crystals before and after microwave exposure. EDS was used to define spatial position of SPION in the polymer matrix of a representative individual microcell.

Microwave RF exposure was performed in a Panasonic 1300 Watt Inverter Technology® Microwave Oven Model NN-SN667W at 130 Watts. The oven was retrofitted with all quartz platforms to reduce/eliminate dipole induction heating from standard glass structures. All containment and experimental material other than water or albumen in contact with the experimental samples was microwave transparent. Containment devices such as test tubes, slides, and cover slips were either quartz or microwave transparent plastics. Microwave oven use was limited to less than 90 minutes per test period to reduce/prevent incidental heating of the oven chamber. A 500 milliliter water "reservoir-load" was maintained within the oven chamber to absorb microwave energy and prevent magnetron damage. All tests were run in an environmentally-controlled room at about 65° F. (about 18.3° C.) and 50% RH.

Microcell aqueous solution sample temperature increases were recorded with a Digi-Tech Digital Thermocouple K-1 probe. The temperature increases showed microcell dispersion is a function of microwave dose. Infrared thermography images of isolated microcells dispersed albumen and aqueous solutions and exposed to 130 Watts microwave radiation were compared and recorded using a FLIR S65 HS infrared camera. Thermographic analysis suggested that SPION filled microcells responded to microwave RF with a more relevant heating profile for hyperthermia therapy than an unfilled microcell in aqueous and albumin solutions. The thermographic analysis showed a sustained generation of heat after microwave RF was discontinued.

Sample vials containing microcells were prepared for microwave exposure. First, 10 milliliters of deionized water containing 0.01% Igepal CO-360 non-ionic surfactant was placed into a 20 ml scintillation vial. Second, 500 milligrams of the microcell sample was added to each vial and dispersed. Duplicate samples for each 130 Watt interval point were prepared. The samples were vortexed to uniformity. The samples included a control of aqueous, 500 grams of Example 2 identified above, and 500 grams of Example 3 identified above. The samples were exposed to 130 Watts of microwave radiation for twelve 30 second intervals with 30 seconds of no exposure between each interval. Temperatures were recorded in the 30 seconds of no exposure using the DigiTec Thermocouple. Samples were averaged and additional thermal imaging thermographic evaluations were performed as isolated samples using the FLIR infrared camera for microcells dispersed in albumen compared to water/surfactant.

Sample vials were prepared in an identical manner and analyzed for API elution. The elution of API from the microcell samples was studied as a passive aqueous diffusion and compared to active microwave induced elution. The active event was induced by 130 Watts microwave RF for 30 second intervals with 30 seconds of no exposure between each interval for a total of 3 minutes. Temperatures were recorded in the 30 seconds of no exposure.

Figure 4:
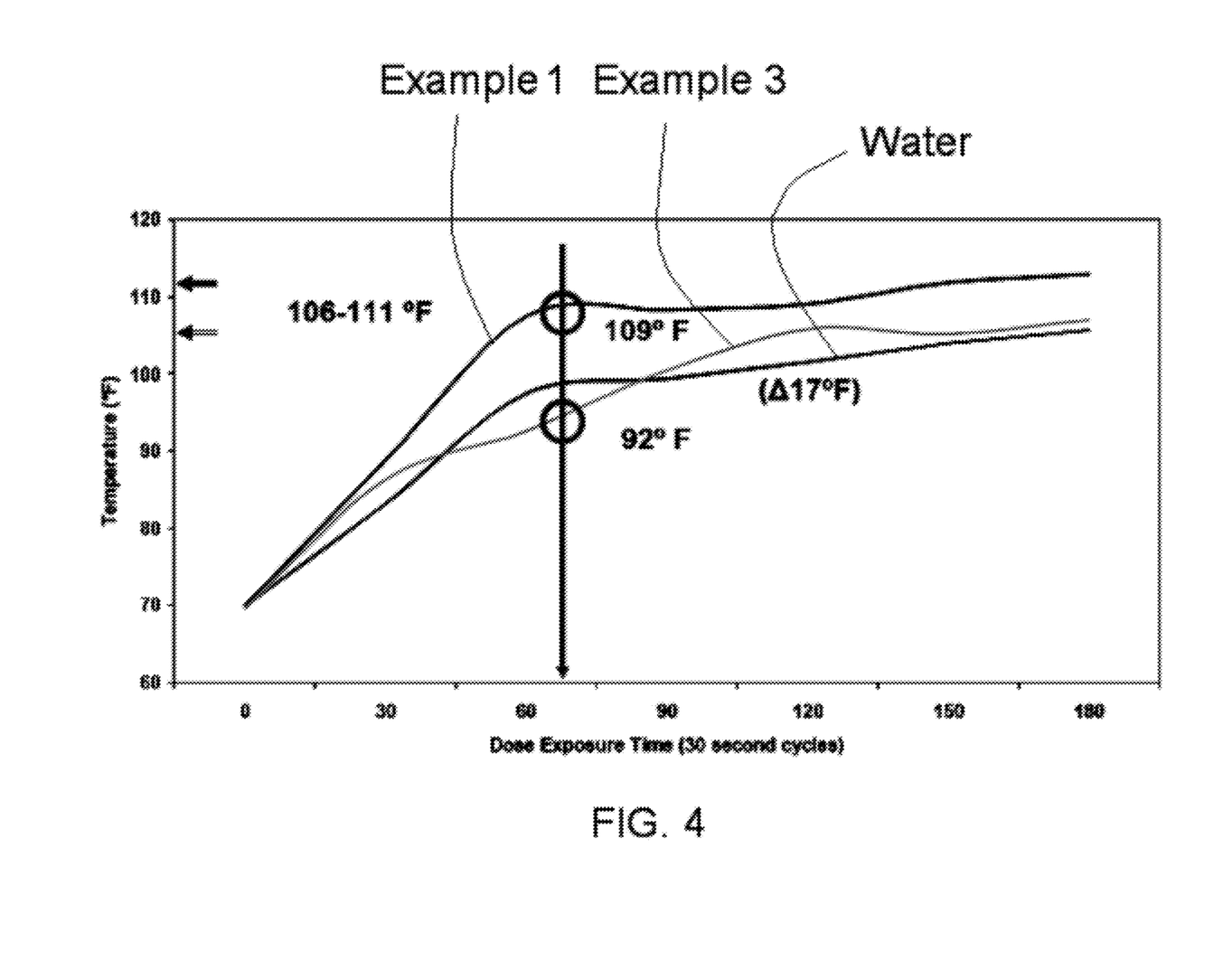
FIG. 4 shows a relationship between temperature and microwave dose exposure time for microcells with differing materials according to several exemplary formulae.

As shown in FIG. 4, after 60 seconds of exposure, a differential of 17° F. was recorded between microcells containing SPION compared to microcells without SPION. SPION containing microcells reached 109° F., whereas microcells without SPION reached 92° F. The 109° F. temperature is within the hyperthermia clinical range for cell death.

As shown in Table 2, about 91% of the 24 hour passive API elution level was reached in 10 minutes. About 84% of the original 1% acetaminophen API in the microcell with SPION was retained in the microcell after processing. Microwave heating of the microcell with SPION may have promoted elution of the API from the microcell matrix. The percentages in Table 2, below, show the amount of API diffused from each sample. Table 2 shows the relative percentage comparison of microcell API diffusion driven by active microwave RF compared to API elution by passive diffusion. The 98° F. 24 hour elution exposure was set for comparison. The table suggests that the 10 minute microwave RF exposure of microcells may elute API within a few percentage of the 24 hour passive diffusion.

TABLE 2

The relative percentage comparison of microcell API elution driven by active microwave radiation showing matrix diffusion

| Temperature/Energy | Time (in minutes) | Relative Percentage based on 24 hours at 98° F. |
|---|---|---|
| 98° F. Passive | Immediate | 11% |
| 98° F. Passive | 10 | 25% |
| 98° F. Passive | 24 | 100% (standard benchmark) |

TABLE 2-continued

The relative percentage comparison of microcell API elution driven by active microwave radiation showing matrix diffusion

| Temperature/Energy | Time (in minutes) | Relative Percentage based on 24 hours at 98° F. |
|---|---|---|
| 130 Watts-Active | 3 | 59% |
| 130 Watts-Active | 5 | 59% |
| 130 Watts-Active | 10 | 91% |

UV analysis of elution samples was determined from a standard curve. Samples were evaluated using a Perkin Elmer UV-Vis Model Lambda 900. Microcell aqueous samples were exposed to radiotherapy and 98° F. (about 36.6° C.) to observe acetaminophen elution from the delivery polymer matrix and compared to aqueous samples exposed to microwave RF for 3 minutes, 5 minutes, and 10 minutes for 30 second intervals with 30 seconds of no exposure between each interval.

Aliquots of aqueous sample were evaluated by UV spectroscopy from a standard curve analysis. Aliquot samples were drawn for UV scanning. Following thermal or microwave exposure, samples were centrifuged at 2500 grams for 5 minutes and swept with a stir bar magnet to ensure complete pick-up of microcells containing SPION and transferred to a quartz cuvette for analysis.

Normal phase 10 centimeter by 5 centimeter plates (specifically, Biotag Flash KP-Sil brand with Indicator TLC plates from VWR) with fluorescent indicator were developed in ethyl acetate. Visualization was either under long wave UV (365 nanometer) exposure or iodine crystal vapor staining. Drummond calibrated micropipettes were used for transfers. Thin layer chromatography was performed as a qualitative test on all samples of materials through processing to insure the integrity of acetaminophen through the handling of the microcell.

FT-IR analysis was performed on Smiths Detection FT-IR Model IlluminatIR® Microscope Smiths Detection ATR FT-IR Model IdentifyIR® Spectrometer. Microcell and fiber acetaminophen migration was followed by FT-IR ATR spectroscopy using a ZnSe crystal or specular reflectance. Because ATR is a surface technique, "path length" is virtual and a function of the ATR crystal refractive index of the contact pressure. All samples were compressed by the automatic stage to ensure full uniform contact at setting 95 (absorbance values are relative to controls). Dry samples of master batch pellets, fiber or dry microcell were placed in a 20 milliliter scintillation vial and exposed to radiotherapy, about 98° F. (about 36.6° C.), and about 110° F. (about 43.3° C.) for 96 hours and then surface scanned for the emergence of acetaminophen bands. Microcell samples were also stimulated as neat samples in the microwave for 90 seconds and examined by ATR. Surfaces of the microcells were analyzed under an SEM for detection of crystals.

Figure 7:
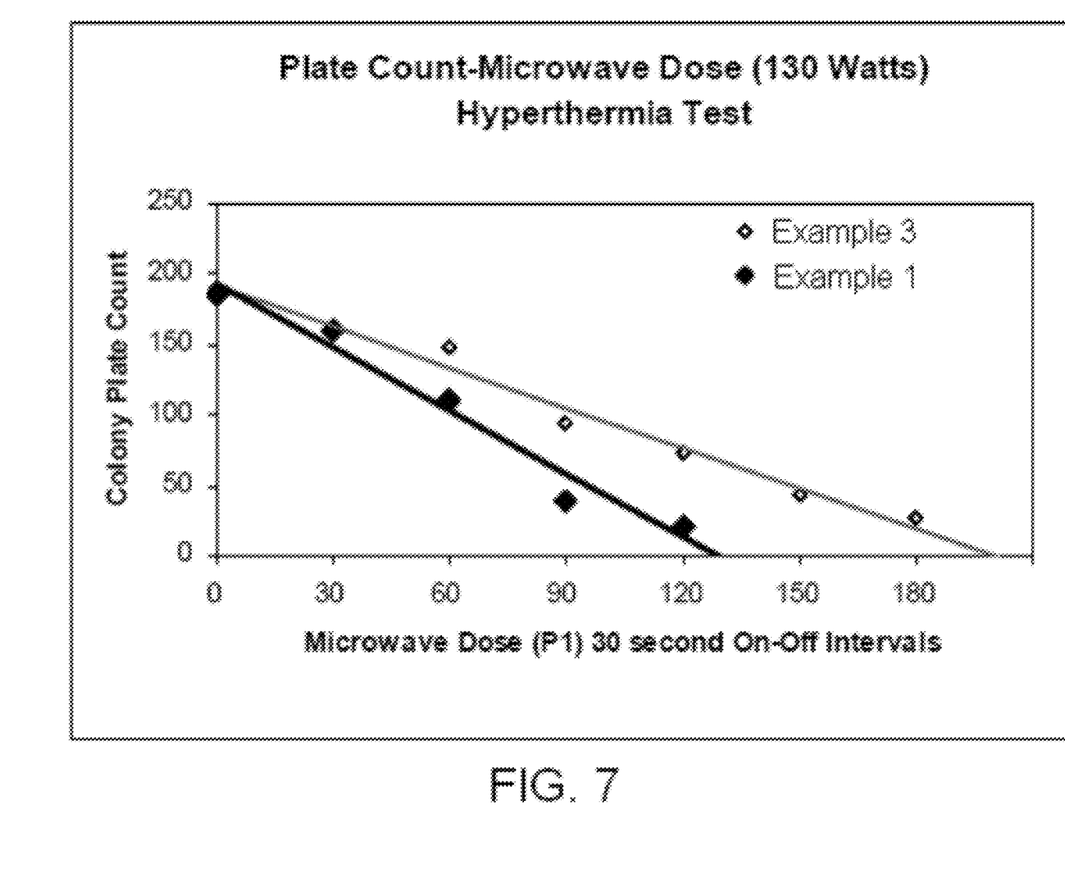
FIG. 7 shows plate counts for exemplary microcell formulae in comparison to microwave dose exposure time.

Yeast culture Saccharomyces cerevisiae ATCC #9763 (from American Type Culture Collection, Rockville, Md.) was incubated in a VWR Scientific Model 1510E incubator at about 74° F. (about 23.3° C.). Cultures were incubated at 74° F. (about 23.3° C.) following each challenge in the fashion of the standard cell viability plate count test. As shown in FIG. 7, microcells containing SPION killed yeast cells with greater efficiency compared to unfilled co-cultured microcells. FIG. 7 shows plate counts for Example 1 and Example 3.

Log phase yeast cultures were prepared in Yeast Peptone Dextrose (YPD) broth or log phase broth transferred to YPD agar or saline solutions. A preliminary evaluation of microwave heating was evaluated for co-culture exposure. Likewise, a preliminary serial dilution standard plate count was performed to determine a workable region. Cultures were diluted to $10^{-4}$ and prepared for microwave exposure. Culture sample optical densities were read on a Thermo Scientific Spectronic® 20 Series Spectrometer as a reference point to growth. Cells from active cultures were harvested and centrifuged. Broth was decanted and cells rewashed four times with saline solution. Washed cells were transferred to 0.85% saline solution and the solution was adjusted to about 0.20 to 0.25. The microcell-yeast sample co-exposures were incubated for 48 hours and plates were counted.

Rabbit/anti-Saccharomyces cerevisiae antibody (from Affinity BioReagents, Golden, Colo.) was used in the preparation of two sets of samples. Example 1, as described above, was prepared for analysis with a first sample of the microcell without antibody and a second sample with antibody in the microcells. Both samples were pretreated to an acid microetch to enhance absorption. About 2 grams of the microcells described in Example 1 were bathed in a solution of 2 milliliters of 0.01 moles HCL in 100 milliliters of deionized water for 15 seconds followed by 5 times rinsing in deionized water. Two 500 milligram samples of microetched microcells were transferred to 20 milliliter vials.

10 milliliters of 2% D-+glucose in 10 millimoles HEPES (GH-solution) were added to the first sample. 100 microliters of anti-Saccharomyces antibody in 100 milliliters of 2% D-+glucose in 10 millimoles HEPES (anti-GH solution) were added to the second sample. Both samples were bathed in solution for two hours at room temperature and then centrifuged. The second sample was washed free of antibody three times in 0.85% saline, and both samples were vacuum dried for 30 minutes with a magnet holder to prevent movement of microcells.

After drying, about 250 milligrams of each sample were transferred into silica well slides and 1 milliliter of active culture in YPD broth was added to each well. Slides were incubated for 30 minutes at about 74° F. (about 23.3° C.) and examined under visible microscopy. Differential absorption of yeast cells to the untreated and treated microcells was analyzed by Nikon L-IM digital light microscopy under blue light filtration, SEM Hitachi® Scanning Electron Microscope Model S-3000N with IXRF Systems Energy Dispersive Spectrometer, and Western blot (described below).

In performing Western blot analysis, the primary antibody was diluted with PBS to a concentration of 0.1 milligrams per milliliter. 25 microliters of NuPAGE LDS Sample Buffer (4×) was added to 75 microliters of diluted antibody. 50 microliters of 1×PBS was added to the microcells and vortexed for about 3 minutes. The solution was then centrifuged at about 14000 rpm for 5 minutes at radiotherapy. 25 microliters of the supernatant was then added to 25 microliters of NuPAGE LDS Sample Buffer (4×). After gel loading was completed, the lower buffer chamber of the Mini-Cell apparatus was filled with about 600 milliliters of MES Running Buffer. The electrodes were aligned on the lid to the gel box and connected to the EPS power supply. The gel running parameters for the 12% Bis-Tris Gels were 200 volts and 12 milliamps for a period of 35 minutes. The blotting parameters were 25 volts and 160 milliamps for a period of 60 minutes.

In another example, PLA Microcells were prepared by HDME with and without SPION. Samples were divided up into two groups. Microcells were placed in PBS solution at pH 6.4, 7.0, and 7.4 and incubated at about 115° F. (about 46.1° C.). Each group remained in solution throughout their exposure except when samples were extracted for FT-IR analysis. Convection oven exposure samples were run first to establish baseline microstructural changes. Microwave samples were suspended from exposure when their spectral changes matched convection oven microstructural changes. The first group incubated in a convection oven over time in solution. Samples of each group were retrieved and examined every 48 hours for a period of 21 days to compare spectral changes. The second group was incubated in solution and periodically exposed to RF pulses of 138 Watts for 1 minute intervals up to 60 minutes. Both the microcell polymer and the isolated solids from the buffered solution were examined by FTIR.

Spectra were taken on a Smith's Identifier ATR FT-IR spectrometer with a diamond ATR crystal from 4000 cm$^{-1}$ to 600 cm$^{-1}$ at 4 cm$^{-1}$ resolution and 64 scans. Data was examined using Gram's software. Samples were air dried for FT-IR examination. Solid microcell samples were placed directly onto the ATR and the spectrum was recorded. Solid samples from liquid residue were also recorded. One milliliter liquid aliquots were transferred to an aluminum dish and the liquid dried to a solid residue. The ATR FT-IR was performed on the aluminum surface. The examples and analytical test suggested that SPIONS in combination with PLA accelerated matrix degradation and that the introduction of RF provided further accelerated matrix degradation.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A microfiber extrudate delivery process comprising:
   identifying a region in an animal;
   medically administering a microfiber extrudate to the region in the animal, the microfiber extrudate comprising:
      a bio-compatible polymer matrix forming a body of the microfiber extrudate;
      a material arranged within the microfiber extrudate body; and
      an active load arranged as a discrete domain within the microfiber extrudate body; and thereafter
   applying exogenous stimulus to the region in the animal from outside of the animal, thereby releasing the active load from the microfiber extrudate body into the region in the animal;
   wherein the step of applying exogenous stimulus to the material to release the active load comprises applying an exogenous stimulus selected from the group consisting of radiofrequency excitation, microwave excitation, terahertz excitation, mid infrared excitation, near infrared excitation, visible excitation, ultraviolet excitation, x-irradiation excitation, magnetic excitation, electron beam irradiation excitation, and combinations thereof;
   wherein the material is a superparamagnetic iron oxide nano-particle.

2. The delivery process of claim 1, wherein the step of medically administering comprises medically administering a microfiber extrudate having a diameter of less than about 110 micrometers.

3. The delivery process of claim 1, wherein the medically administered microfiber extrudate comprises the material arranged in at least one discrete domain.

4. The delivery process of claim 1, wherein the medically administered microfiber extrudate has a size and geometry substantially similar to a red blood cell or white blood cell.

5. The delivery process of claim 1, wherein the medically administered microfiber extrudate is disc-shaped.

6. The delivery process of claim 1, wherein the medically administered microfiber extrudate has a transverse thickness of less than about 12 micrometers.

7. The delivery process of claim 1, wherein the active load of the medically administered microfiber extrudate comprises an active pharmaceutical ingredient.

8. The delivery process of claim 7, wherein the active pharmaceutical ingredient includes acetaminophen.

9. The delivery process of claim 1, wherein the active load of the medically administered microfiber extrudate comprises an antibody.

10. The delivery process of claim 1, wherein the active load of the medically administered microfiber extrudate comprises an anti-VEGH.

11. The delivery process of claim 1, wherein the material of the medically administered microfiber extrudate is a radiosensitive chemotherapeutic agent.

12. The delivery process of claim 1, wherein the active load of the medically administered microfiber extrudate is a non-radiosensitive chemotherapeutic agent.

13. The delivery process of claim 1, wherein the bio-compatible polymer matrix of the medically administered microfiber extrudate comprises a polyglycolide copolymer.

14. A microfiber extrudate delivery process comprising:
   identifying a region in a human;
   medically administering a microfiber extrudate to the region in the human, the microfiber extrudate comprising:
      a polyglycolide copolymer base bio-compatible polymer matrix forming a body of the microfiber extrudate;
      a paramagnetic material arranged within the microfiber extrudate body; and
      an active pharmaceutical ingredient arranged as a discrete domain within the microfiber extrudate body; and thereafter
   applying radio-frequency stimulation to the region in the human from outside of the human to stimulate the paramagnetic material and release the active load from the microfiber extrudate body into the region in the human;
   wherein the microfiber extrudate is constructed from a micro-extrusion fiber spinning process;
   wherein the step of applying exogenous stimulus to the material to release the active load comprises applying an exogenous stimulus selected from the group consisting of radiofrequency excitation, microwave excitation, terahertz excitation, mid infrared excitation, near infrared excitation, visible excitation, ultraviolet excitation, x-irradiation excitation, magnetic excitation, electron beam irradiation excitation, and combinations thereof;
   wherein the material is a superparamagnetic iron oxide nano-particle.

15. The microfiber extrudate delivery process of claim 14, wherein the medically administered microfiber extrudate further comprises an anti-body.

* * * * *